(12) United States Patent
Jussel

(10) Patent No.: US 9,920,994 B2
(45) Date of Patent: Mar. 20, 2018

(54) DENTAL PRESSING FURNACE

(71) Applicant: Ivoclar Vivadent AG, Schaan (LI)

(72) Inventor: Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 195 days.

(21) Appl. No.: 14/770,187

(22) PCT Filed: Feb. 6, 2014

(86) PCT No.: PCT/EP2014/052279
§ 371 (c)(1),
(2) Date: Nov. 9, 2015

(87) PCT Pub. No.: WO2014/131588
PCT Pub. Date: Sep. 4, 2014

(65) Prior Publication Data
US 2016/0069614 A1    Mar. 10, 2016

(30) Foreign Application Priority Data
Feb. 27, 2013  (EP) .................................... 13157042

(51) Int. Cl.
*A61C 13/20* (2006.01)
*F27B 17/02* (2006.01)
(Continued)

(52) U.S. Cl.
CPC ............. *F27B 17/025* (2013.01); *A61C 13/20* (2013.01); *F27B 5/10* (2013.01); *F27B 5/18* (2013.01); *F27D 21/0014* (2013.01)

(58) Field of Classification Search
CPC .......... A61C 13/20; F27B 17/025; F27B 5/10; F27D 19/00
See application file for complete search history.

(56) References Cited

U.S. PATENT DOCUMENTS 5,302,104 A * 4/1994 Ueda ...................... A61C 13/04
                                                   249/54
6,252,202 B1 * 6/2001 Zychek ................. F27B 17/025
                                                   219/385
(Continued)

FOREIGN PATENT DOCUMENTS

DE    102006004433 A1    8/2007
DE    102006004433 B4 *  4/2013    ............. A61C 13/20
(Continued)

Primary Examiner — Gregory A Wilson
(74) Attorney, Agent, or Firm — Ann M. Knab; Thad McMurray

(57) ABSTRACT

The invention relates to a dental pressing furnace for producing a dental restoration element in a muffle (8) by heating and pressing a blank (14). The dental pressing furnace comprises a combustion chamber (6), comprising at least one guide opening (11) that is opened towards the outside and a pressing stamp (4) guided in the guiding opening (11) and protruding into the combustion chamber (6) for applying pressing force to the heated blank (14) in the muffle (8). A temperature transmitter (36) guided at least in part by the pressing stamp (4) is configured to guide a temperature (50) of the blank (14) in the combustion chamber (6) from said combustion chamber, and a temperature sensor (34) connected to the temperature transmitter (36) outside of the combustion chamber captures the temperature (50).

14 Claims, 3 Drawing Sheets

(51) Int. Cl.
*F27D 21/00* (2006.01)
*F27B 5/10* (2006.01)
*F27B 5/18* (2006.01)

(56) References Cited

U.S. PATENT DOCUMENTS

| | | | | |
|---|---|---|---|---|
| 6,303,059 | B1* | 10/2001 | Foser | A61C 13/20 |
| | | | | 264/16 |
| 7,325,433 | B2* | 2/2008 | Foser | A61C 13/20 |
| | | | | 264/16 |
| 8,232,506 | B2 | 7/2012 | Jussel | |
| 8,742,298 | B2* | 6/2014 | Jussel | F27B 17/025 |
| | | | | 219/390 |
| 9,022,763 | B2* | 5/2015 | Miller | A61C 13/20 |
| | | | | 264/16 |
| 2009/0155736 | A1* | 6/2009 | Vekoerrer | A61C 13/206 |
| | | | | 433/34 |
| 2009/0246739 | A1 | 10/2009 | Jussel et al. | |
| 2013/0029281 | A1* | 1/2013 | Jussel | A61C 13/20 |
| | | | | 432/32 |

FOREIGN PATENT DOCUMENTS

| | | |
|---|---|---|
| EP | 1978321 A1 | 10/2008 |
| EP | 2105691 A1 | 9/2009 |
| WO | 03011168 A1 | 2/2003 |

\* cited by examiner

DENTAL PRESSING FURNACE

CROSS-REFERENCE TO RELATED APPLICATIONS

This application is a National Stage application of International Patent Application No. PCT/EP2014/052279 filed on Feb. 7, 2014, which claims priority to European Patent Application No. 13157042.6 filed on Feb. 27, 2013, the disclosures of which are incorporated herein by reference in their entirety.

TECHNICAL FIELD

The invention concerns a dental pressing furnace with a pressing stamp, in accordance with the preamble of Claim 1.

BACKGROUND OF THE INVENTION

From DE 100 39 147 A1, a dental pressing furnace with a combustion chamber and a muffle accommodated in the combustion chamber with a cavity in the shape of a dental restoration element is known. Inside the combustion chamber, a blank in the form of a ceramic blank accommodated in the muffle can be heated up to a pressing temperature at which the blank becomes viscous, in order to press it into the cavity with the help of a pressing stamp. In order to determine the optimum moment for starting the pressing process, at which the blank has reached the pressing temperature, a thermal element is accommodated in the muffle. Depending on the starting temperature of the dental pressing furnace or the muffle, however, mispresses result from this process time and again.

SUMMARY

In contrast to this, the invention has the task of improving the dental pressing furnace in accordance with the claims and avoiding mispresses if possible.

The task is solved, in accordance with the invention, by the features of Claim 1. Preferred further embodiments are the subject of the subordinate Claims.

In accordance with one aspect of the invention, a dental pressing furnace for producing a dental restoration element comprises a combustion chamber which is opened towards the outside with the help of at least one guiding opening, in which combustion chamber the dental restoration element can be produced in a muffle by means of heating and pressing a blank, and a pressing stamp guided in the guiding opening and protruding into the combustion chamber for applying pressing force to the heated blank in the muffle. The dental pressing furnace mentioned further comprises a temperature transmitter guided at least in part by the pressing stamp which is configured to guide a temperature of the blank in the combustion chamber from said combustion chamber, and a temperature sensor connected to the temperature transmitter outside of the combustion chamber for capturing the temperature.

The dental pressing furnace in accordance with the invention has the particular advantage that the temperature can be captured directly in the immediate proximity of the blank when the blank is pressed. Although it is possible with the help of the above-mentioned thermal element which is accommodated in the muffle to capture the temperature in the combustion chamber, it is of disadvantage that this thermal element is subjected to high temperature loads and mechanical loads in the combustion chamber of the dental pressing furnace, for which reason very cost-intensive sheath or jacket thermocouples must be employed here in order to allow a tolerably permanent use. Irrespective of this, the handling of this thermal element which can be accommodated in the muffle is very problematic too. The dental technician needs to always position the muffle over this thermal element since the thermal element creates a positive connection between the combustion chamber and the muffle of the dental pressing furnace in a fashion like in a tongue-and-groove connection, which needs to be penetrated by the thermal element.

The dental pressing furnace in accordance with the invention is distinctly improved compared with this, within the scope of which furnace the temperature of the blank can be captured sensorically directly and locally, can be evaluated and then guided out of the combustion chamber. Therefore it is suggested not to capture the temperature of interest sensorically directly and locally at the blank for the dental restoration element to be produced, but rather outside of the combustion chamber. For this purpose, the temperature transmitter is provided which transmits the temperature of the blank or an element which is in immediate connection with the blank, such as the pressing stamp, out of the combustion chamber and makes it possible to measure the temperature outside of the combustion chamber.

Different from a thermal element, the temperature transmitter, however, needs not be provided in one piece, for the temperature to be transmitted can permeate the individual interfaces between the segments of the optical conductor in case of a temperature transmitter which is constructed out of a number of segments. Therefore the temperature transmitter, in contrast to the above-mentioned thermal element, does not necessarily have to form a positive connection between individual elements of the dental pressing furnace which it penetrates. Subsequently, the sensor device for capturing the temperature, does not obstruct any longer the individual elements accommodated in the combustion chamber, such as muffle and pressing stamp, in their arrangement, as a result of which the handling of the dental pressing furnace mentioned is noticeably facilitated, because the dental technician is no longer restricted by the temperature sensor in positioning the elements of the dental pressing furnace.

The temperature transmitter can basically be provided in any form desired and can work according to any principle of temperature transmission desired, such as, for example, conduction of heat, thermal radiation or heat convection. In a particularly favourable fashion, the temperature transmitter is an optical conductor for guiding the temperature in the form of thermal radiation, such that the temperature of the blank can be captured based on the thermal radiation guided outside.

Surprisingly mispresses can be avoided in accordance with the present invention, probably because the starting temperature of the blank and also the temperature profile can be precisely measured in a stable fashion also over a long time, and the output signal of the temperature sensor in accordance with the invention can be used as a control variable for controlling the furnace.

In a further embodiment of the dental pressing furnace in accordance with the invention, the optical conductor is coated in parallel with a light guiding direction of the optical conductor. Within the scope of this coating, it is effectively prevented that the thermal radiation transmitted by the optical conductor is diluted by thermal radiation from the combustion chamber or the heating element, respectively, entering from the side, which further improves temperature measurement.

In a preferred further embodiment of the dental pressing furnace in accordance with the invention, the optical conductor is made out of quartz glass or sapphire. Such materials do not only have a favourable light conductivity, but are also mechanically stable, such that the pressing stamp could, at least in portions, be entirely formed out of the optical conductor alone. Alternatively, a drilling, a cavity, or another passage opening can be used as an optical conductor as well.

In an additional further embodiment of the dental pressing furnace in accordance with the invention, the pressing stamp comprises a basic body with a force absorption surface for absorbing the pressing force and with a pressing surface for applying the pressing force to the blank, which pressing surface is positioned opposite of the force absorption surface observed in the direction of the pressing force, wherein the optical conductor extends from the force absorption surface towards the pressing surface. Herein, the optical conductor can remain entirely jacketed by the pressing stamp. The closer, however, the optical conductor inside the pressing stamp is guided towards the force absorption surface, and thus towards the contact surface with the blank to be pressed, the more precise are the measurement results for the temperature of the blank which are captured with the help of the optical temperature sensor via the optical conductor.

In a particular further embodiment of the dental pressing furnace in accordance with the invention, the optical conductor penetrates the basic body from the force absorption surface towards the pressing surface. Although the results of the temperature measurement within the scope of the dental pressing furnace mentioned are already satisfactory when the blank is separated from the optical conductor by pollutions or a wall of the pressing stamp, the best measurement results are only achieved with the help of the optical conductor if the optical conductor is guided directly up to the blank, such that the optical conductor entirely penetrates the pressing stamp.

In another embodiment of the dental pressing furnace in accordance with the invention, the basic body of the pressing stamp is made up of a pressing rod with the force absorption surface and a contact piston with the pressing surface. In this fashion, materials of the pressing stamp can be optimally matched with the requirements at the individual surfaces. For instance, the contact piston could be an aluminium oxide piston which prevents pollutions from accumulating at the pressing rod. In addition, aluminium oxide is brittle and has a coefficient of expansion that is within the range of coefficients of expansion of established materials which are used as blanks for the production of the dental restoration element.

Even if pollutions develop at the boundary surface between the temperature transmitter or the contact piston and the blank, these usually have the same temperature as the blank. So if the temperature transmitter abuts there, the temperature of the blank will still be transmitted.

In an alternative further embodiment of the dental pressing furnace in accordance with the invention, the pressing rod and the contact piston are connected with each other with the help of a positive connection acting in the direction of the pressing force. If the optical conductor is formed out of two parts, with one part being guided through the pressing rod, and the other part being guided through the contact piston, the positive connection acting in the direction of the pressing force will improve the optical transition between the two parts of the optical conductor, in particular with the pressing force applied, and will support temperature measurement in this fashion.

In a preferred further embodiment of the dental pressing furnace in accordance with the invention, the positive connection additionally acts transversely to the direction of the pressing force, such that the contact piston and the pressing rod are accommodated in a pre-determined position relative to one another, in which in particular within the scope of the two-part construction of the optical conductor mentioned above, the two parts can be brought in safe contact with each other in order to produce an optical passage for the transmission of thermal radiation.

In an additional further embodiment of the dental pressing furnace in accordance with the invention, the temperature sensor can be an optical temperature sensor if an optical conductor is used as the temperature transmitter.

In an alternative further embodiment of the dental pressing furnace in accordance with the invention, the dental pressing furnace comprises another temperature sensor engaging with the combustion chamber for capturing a room temperature inside the combustion chamber. This room temperature can then, for example, be used for controlling the temperature inside the furnace, wherein it is also possible to monitor errors.

BRIEF DESCRIPTION OF THE DRAWINGS

The characteristics, features and advantages of this invention described above as well as the manner in which these are achieved become more obvious and more clearly understandable in connection with the subsequent description of the exemplary embodiments which are explained in more detail in connection with the Figures, which show.

DETAILED DESCRIPTION

In the Figures, equal technical elements are marked with equal reference numbers and are described only once.

Figure 1:
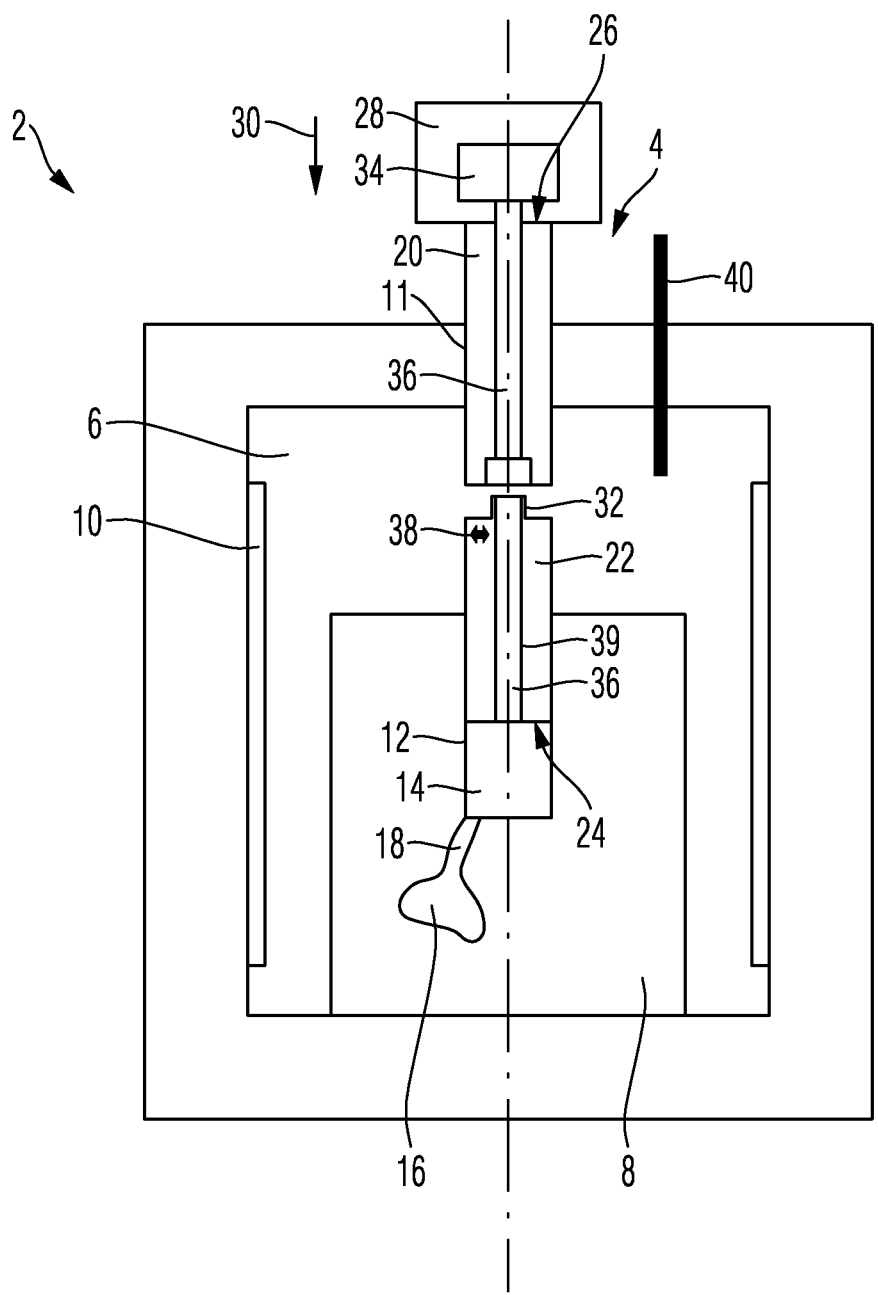
FIG. 1 a dental pressing furnace with a pressing stamp in accordance with a first exemplary embodiment.

Reference is made to FIG. 1 which shows a dental pressing furnace 2 with a pressing stamp 4 in accordance with a first exemplary embodiment.

Dental pressing furnace 2 is provided, in a basically known fashion, with a combustion chamber 6 for accommodation of a muffle 8 as well as a heating element 10 arranged inside combustion chamber 6 for the purpose of heating up combustion chamber 6 and thus muffle 8. Combustion chamber 6 is provided with a guiding opening 11 guiding pressing stamp 4.

Muffle 8 is provided with an accommodation space 12 in which a blank 14 for producing a dental restoration element is accommodated. Muffle 8 is designed as an investment materials muffle in whose accommodation space 12 blank 14, for example in the form of a blank, in particular of a ceramic blank, is accommodated.

In muffle 8, at least one cavity 16 is provided in the shape of the dental restoration element to be produced. Cavity 16 is connected with accommodation space 12 via a connection channel 18. At the side opposite connection channel 18, accommodation space 12 is closed by pressing stamp 4.

Pressing stamp 4 is in the present embodiment constructed of two pieces, one pressing rod 20 and one contact piston made out of aluminium oxide and referred to as AlOx piston 22 in the following. While AlOx piston 22 is in direct contact at a pressing surface 24 with blank 14 which is to be deformed into the dental restoration element, pressing rod 20 is provided with a force absorption surface 26 on which a drive unit 28, for instance in the form of a stepper or multi-phase motor, acts in order to move pressing rod 20 in a pressing direction 30 into the direction of blank 14. AlOx piston 22 and pressing rod 20 can be connected with each other with the help of a positive connection 32, which acts in the pressing direction 30, in order to transfer a pressing force of drive unit 28 to blank 14. Furthermore, positive connection 32 acts in a transverse direction of pressing direction 30 in order to precisely align pressing rod 20 and AlOx piston 22 relative to one another.

In the operation of dental pressing furnace 2, for the production of the dental restoration element, muffle 8 which is accommodated in combustion chamber 6, and thus blank 14 held in accommodation space 12, is heated up with the help of heating element 10 until blank 14 has reached a viscous state in which it can be pressed into cavity 16 with the help of pressing stamp 4 via connection channel 18. Then, pressing stamp 4 is moved in the pressing direction 30 with the help of drive unit 28 which acts on force absorption surface 26. Pressing stamp 4, and thus the heated, viscous blank 14 at pressing surface 24, is subjected to the driving force from drive unit 28 and is moved into cavity 16 via connection channel 18. When cavity 16 has been completely filled with the material of blank 14, the dental restoration element 14 which has been created inside cavity 16 is cooled down.

At the beginning of the pressing process, however, it must be guaranteed that blank 14 has been sufficiently heated and is therefore sufficiently viscous for being pressed.

For this purpose, dental pressing furnace 2 comprises, in accordance with the invention, an optical temperature sensor 34 arranged in the area of drive unit 28, and an optical conductor in the form of a light guide 36 which in the current embodiment is blank 14 in accommodation space 12 and optically connects optical temperature sensor 34 with each other. Heated blank 14 radiates a not depicted thermal radiation which is collected by light guide 36 and guided on to optical temperature sensor 34 arranged outside of the combustion chamber. In this fashion, optical temperature sensor 34 can determine outside of the combustion chamber the optimal moment for starting drive unit 28 and thus for production of the dental restoration element based on the temperature of blank 14. The temperature of blank 14 is constantly monitored during the pressing process as well.

This results in the advantage that the firing and pressing process, respectively, can be considerably accelerated. The combustion chamber can first be heated up to a temperature which is above the pressing temperature. This results in a faster transmission of heat through the muffle to the blank, and the fact that the temperature is captured at the blank guarantees that said temperature is not above the pressing temperature. Shortly before the pressing temperature has been reached, the temperature inside the combustion chamber is reduced, which is done to a value that corresponds to the pressing temperature, or possibly also to a temperature below this. As a result of the muffle's thermal capacity, its residual heat is still transferred to the blank, ad and the fact that the temperature at the blank is precisely captured makes it possible to prevent it from being heated to a temperature above the pressing temperature. The moment of pressing is precisely determined by this, and the pressing process is triggered immediately when the pressing temperature has been reached.

In the present embodiment, light guide 36 is open at the position of transition, but can be assembled in a positive connection together with pressing rod 20 and AlOx piston 22 in pressing direction 30. The interface between the two parts of light guide 36 in the area of transition 32 only has an influence on the thermal radiation from blank 14 towards optical temperature sensor 34 that is negligible for temperature measurement.

This means that the inaccuracies in the positioning of pressing rod 20 to AlOx piston 22 can be neglected within the scope of temperature measurement. For instance, pollutions accumulating between blank 14 and AlOx piston 22 on the temperature of blank 14, such that they do not impair the temperature measurement at the blank.

In order to use AlOx piston 22 always in a pre-defined direction between pressing rod 20 and blank 14, alternatively to the positive connection 32 present, or transition, additionally to that a marking 38 can be arranged at AlOx piston 22 which can, for example, show which side of AlOx piston 22 must be oriented towards pressing rod 20.

Finally the light guide can be provided with a reflecting coating 39 transversely to pressing direction 30, which prevents thermal radiation from combustion chamber 6 from entering into the light guide, which does not belong to the thermal radiation from blank 14.

For controlling the temperature inside combustion chamber 6, a basically known thermal control element 40 can be provided. In a particularly favourable fashion, optical temperature sensor 34 provides, in addition to the temperature inside combustion chamber 6 captured with the help of thermal control element 40, a second piece of temperature information, with the help of which the temperature captured by thermal control element 40 can, for instance, be made plausible, and with the help of which also an improved temperature control can be achieved, and as a further result, the process as a whole is accelerated.

Figure 2:
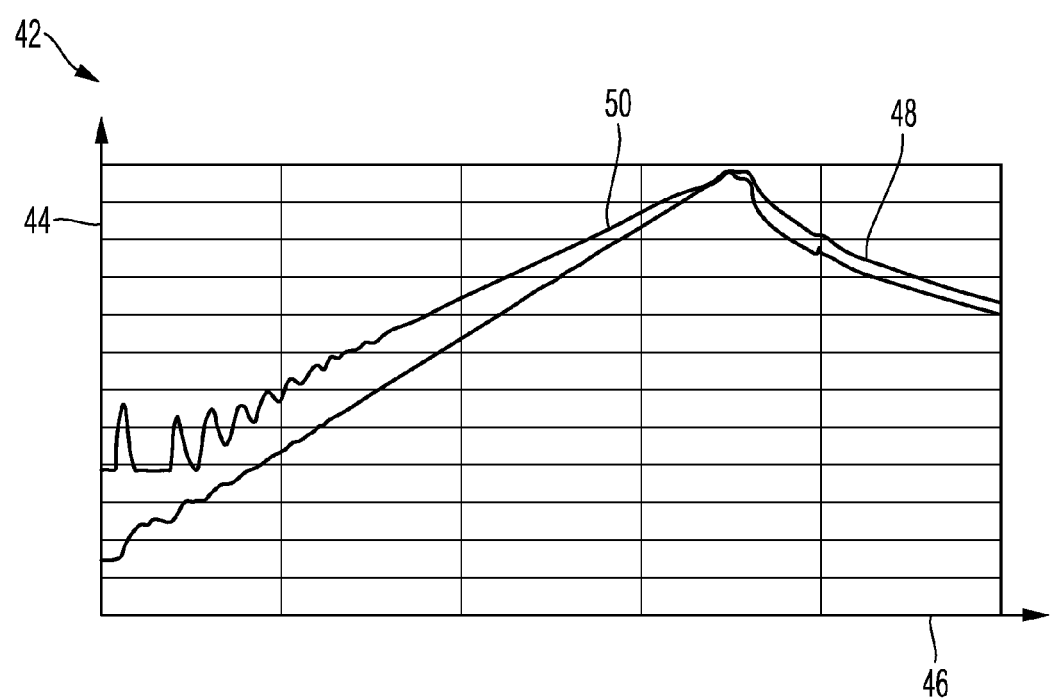
FIG. 2 a temperature diagram with temperature profiles at different positions in the dental pressing furnace.

In FIG. 2, by way of example, combustion chamber temperature 48 from thermal control element 40 and materials temperature 50 from optical temperature sensor 34 are contrasted in a diagram 42 with temperatures 44 plotted over time 46.

As can be seen, a time lag results between combustion chamber temperature 48 and temperature 50 of the blank measured with the help of sensor 34.

Figure 3:
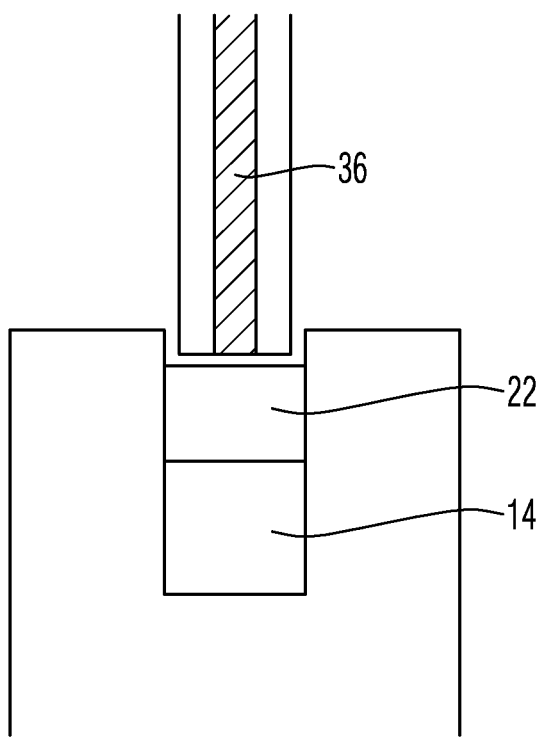
FIG. 3 a schematic view of another embodiment of the invention, in a detailed depiction.

In FIG. 3, details of a modified embodiment of a dental pressing furnace 2 are depicted. Light guide 36 extends here as well through pressing rod 20. Between pressing rod 20 and blank 14, a contact piston made of quartz glass or another material that is a good thermal conductor is put into practice, which material accepts the temperature of blank 14 and insofar makes possible a precise determination of the temperature of the blank.

Thermal conductivity of contact piston 22, in any case, is distinctly higher than, for instance three times as high as, thermal conductivity of the muffle which surrounds blank 14 and contact piston 22.

The invention claimed is:

1. Dental pressing furnace for producing a dental restoration element in a muffle (8) by heating and pressing a blank (14), with a combustion chamber (6), and a pressing stamp (4) guided in a guiding opening (11) for applying pressing force to the heated blank (14) in the muffle (8), characterised in that a temperature transmitter (36) guided at least in part by the pressing stamp (4) is configured to guide the temperature (50) of the blank (14) in the combustion chamber (6) from said combustion chamber, and a temperature sensor (34) connected to the temperature transmitter (36) outside of the combustion chamber captures the temperature (50).

2. Dental pressing furnace in accordance with claim 1, characterised in that the temperature transmitter (36) is an optical conductor (36) for guiding the temperature (50) of the blank (14) in the form of thermal radiation, and that the temperature (50) of the blank (14) can be captured based on the thermal radiation guided out.

3. Dental pressing furnace in accordance with claim 2, characterised in that the optical conductor (36) is coated (39) in parallel with a light guiding direction of the optical conductor (36).

4. Dental pressing furnace in accordance with claim 2, characterised in that the optical conductor (36) is made out of quartz glass or sapphire, or consists of a passage opening.

5. Dental pressing furnace in accordance with claim 1, characterised in that the pressing stamp (4) is provided with a basic body with a force absorption surface (26) for absorbing the pressing force and with a pressing surface (24) for applying the pressing force to the blank (14), which pressing surface is positioned opposite of the force absorption surface (26) observed in the direction (30) of the pressing force, and wherein the temperature transmitter (36) extends from the force absorption surface (26) towards the pressing surface (24).

6. Dental pressing furnace in accordance with claim 5, characterised in that the temperature transmitter (36) penetrates the basic body from the force absorption surface (26) towards the pressing surface (24).

7. Dental pressing furnace in accordance with claim 5, characterised in that the basic body is made up of a pressing rod (20) with the force absorption surface (26) and a contact piston (22) with the pressing surface (24).

8. Dental pressing furnace in accordance with claim 7, characterised in that the pressing rod (20) and the contact piston (22) are connected with each other with the help of a positive connection (32) acting in the direction (30) of the pressing force, and the contact piston (22) is provided with a marking with the help of which the position of the contact piston in relation to the blank (14) can be identified.

9. Dental pressing furnace in accordance with claim 1, characterised in that the temperature sensor (34) is an optical temperature sensor (34) and captures the temperature of the blank (14) during the phase of heating of the blank (14), during the pressing movement and also during the pressing process.

10. Dental pressing furnace in accordance with claim 1, characterised in that the temperature of the blank (14) captured by the temperature sensor (34) triggers the pressing process.

11. Dental pressing furnace in accordance with claim 1, characterised by a drive unit (28) which creates the pressing force to be applied to the heated blank (14) in the muffle (8), which is arranged outside of the combustion chamber and adjacent to the temperature sensor (34).

12. Dental pressing furnace in accordance with claim 11, characterised in that the temperature transmitter (36) extends beyond the pressing stamp (4), and the pressing drive unit (28) surrounds the temperature sensor (34).

13. Dental pressing furnace in accordance with claim 1, characterised in that the temperature transmitter (36) abuts against the side of the blank (14) positioned opposite of the temperature sensor (34) or terminates at a position which is spaced apart from the blank (14) by less than 1 mm.

14. Dental pressing furnace in accordance with claim 1, characterised by another temperature sensor (40) protruding into the combustion chamber (6) for capturing a room temperature (48) in the combustion chamber (6).

* * * * *